United States Patent [19]

Condon et al.

[11] Patent Number: 5,076,835
[45] Date of Patent: Dec. 31, 1991

[54] ARYLOXYSPIROALKYLINDOLINONE HERBICIDES

[75] Inventors: Michael E. Condon, Lawrenceville; Gary M. Karp, Plainsboro, both of N.J.; Jeffrey H. Birk, Morrisville, Pa.

[73] Assignee: America Cyanamid Company, Stamford, Conn.

[21] Appl. No.: 531,712

[22] Filed: May 31, 1990

[51] Int. Cl.$^5$ .................. C07D 401/12; C07D 209/96; A01N 43/40; A01N 43/38
[52] U.S. Cl. .......................................... 71/96; 71/94; 546/15; 548/411; 564/443
[58] Field of Search .............. 548/411; 546/15; 71/96, 71/94

[56] References Cited

U.S. PATENT DOCUMENTS 4,911,754  3/1990  Hunt et al. ............................... 71/96

OTHER PUBLICATIONS

Aoki, Chem. Abs. 112, 108412f (1989).

Primary Examiner—Mark L. Berch
Attorney, Agent, or Firm—John W. Hogan, Jr.

[57] ABSTRACT

There are provided aryloxy-1'-(substituted)-spiro[cycloalkane-1,3'-indolin]-2'-one compounds, their herbicidal use, particularly for the selective control of undesirable plant species in the presence of cereal crops such as rice and wheat, and a method for the preparation thereof.

17 Claims, No Drawings

ARYLOXYSPIROALKYLINDOLINONE HERBICIDES

BACKGROUND OF THE INVENTION

Cereal crops such as rice and wheat are of worldwide economic importance. There is a recognized need in agronomic practice for effective herbicidal agents which can be used in the presence of important agricultural crops without causing undue injury to said crops. Without adequate control, undesirable plant species can eliminate or reduce the yield of crops and diminish the efficient production and harvest of crops. Selectivity of the herbicide is especially important in order to provide excellent control of undesirable weed species in the presence of the crop.

SUMMARY OF THE INVENTION

The present invention provides aryloxy-1'-(substituted)-spiro[cycloalkane-1,3'-indolin]-2'-one compounds of formula I

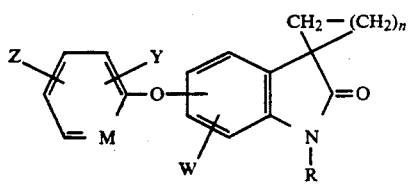

wherein
M is N or CX;
X, Y and Z are each independently hydrogen, halogen, CN, $NO_2$ or $C_1$-$C_6$ alkyl optionally substituted with one or more halogens;
W is hydrogen, halogen, CN, $NO_2$, $C_1$-$C_6$ alkoxy, $C_1$-$C_6$ carboalkoxy or $C_1$-$C_6$ alkyl optionally substituted with one or more halogens or $OR_1$ groups with the proviso that at least two of W, X, Y and Z must be other than CN or $NO_2$;
n is an integer of 1, 2, 3, 4 or 5;
R is $C_3$-$C_6$ alkenyl, $C_3$-$C_6$ alkynyl or $C_1$-$C_6$ alkyl optionally substituted with one or more of the following groups: halogen, $OR_1$, $COOR_1$ or $NH_2$;
$R_1$ is hydrogen or $C_1$-$C_4$ alkyl.

A preferred group of aryloxyspiroalkylindolinone compounds may be illustrated as formula II

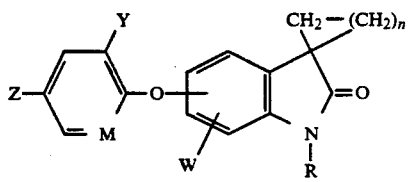

wherein M is CX and W, X, Y, Z, R and n are as described above for formula I.

Surprisingly, it has now been found that the aryloxypiroalkylindolinones as hereinabove described demonstrate a high degree of selectivity towards cereal crops such as rice and wheat while providing excellent control of a wide variety of undesirable broadleaf and grass plant species.

DETAILED DESCRIPTION OF THE INVENTION

The present invention relates to aryloxyspiroindolinone compounds of formula I

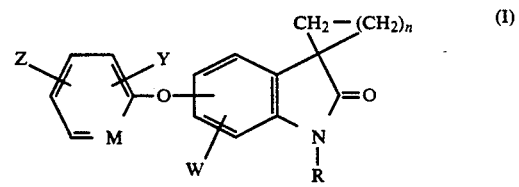

wherein
M is N or CX;
X, Y and Z are each independently hydrogen, halogen, CN, $NO_2$ or $C_1$-$C_6$ alkyl optionally substituted with one or more halogens;
W is hydrogen, halogen, CN, $NO_2$, $C_1$-$C_6$ alkoxy, $C_1$-$C_6$ carboalkoxy or $C_1$-$C_6$ alkyl optionally substituted with one or more halogens or $OR_1$ grops with the proviso that at least two of W, X, Y and Z must be other than CN or $NO_2$;
n is an integer of 1, 2, 3, 4 or 5;
R is $C_3$-$C_6$ alkenyl, $C_3$-$C_6$ alkynyl or $C_1$-$C_6$ alkyl optionally substituted with one or more of the following groups: halogen, $OR_1$, $COOR_1$ or $NH_2$;
$R_1$ is hydrogen or $C_1$-$C_4$ alkyl.
The term halogen designates F, Cl, Br or I.
A preferred embodiment of the invention is a compound of formula II

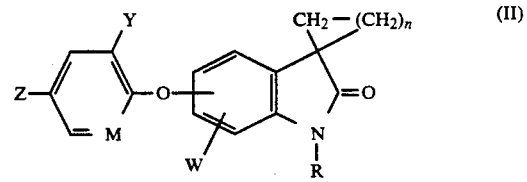

wherein M is CX and W, X, Y, Z, r and n are as described for formula I.

Compounds of formula I may be prepared as shown in Flow Diagram I.

FLOW DIAGRAM I

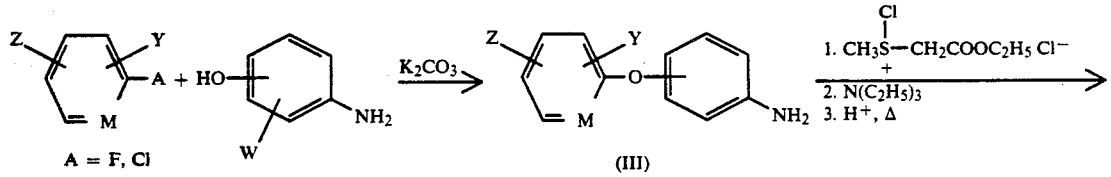

-continued
FLOW DIAGRAM I

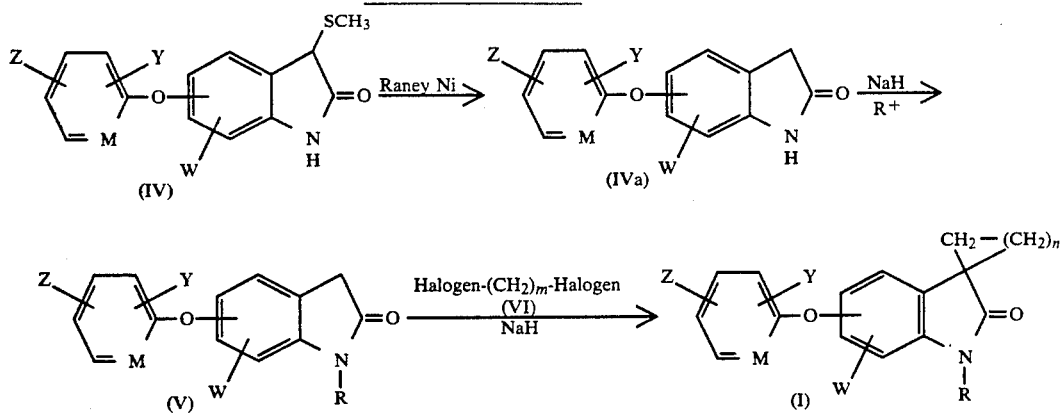

The appropriately substituted arylchloride or arylfluoride may be reacted with a suitably substituted aminophenol in the presence of a base such as an alkali metal carbonate and a polar solvent such as acetonitrile to give the aryloxyaniline compound of formula III. The formula III intermediate is reacted sequentially with the chlorosulfonium salt of ethyl methylthioacetate in the presence of at least one equivalent of a base such as triethylamine and a non-protic solvent such as methylene chloride at a temperature range of about $-78°$ C. to $-30°$ C., at least one additional equivalent of a base at said ice bath temperatures and, after warming to room temperature and removing the solvent and any excess base, heated at reflux temperatures in the presence of a catalytic amount of an acid such as p-toluenesulfonic acid in an aromatic hydrocarbon or chlorinated aromatic hydrocarbon solvent with a boiling point range of about 90° C. to 150° C. to give the aryloxymethylthioindolinone compound of formula IV. Said formula IV compound may be desulfurized in the presence of Raney Nickel and a protic solvent or solvent mixture such as a loweralkyl alcohol or an alcohol and dimethylformamide to give the corresponding aryloxyindolinone intermediate and alkylated using a suitable alkylating agent such as dialkylsulfate in the presence of at least one equivalent of an alkali metal hydride and a suitable solvent to give the aryloxyindolinone compound of formula V. Said formula V indolinone can then be bis-alkylated by using the appropriate dihaloalkane of formula VI wherein m is an integer of n+1 and at least 2 equivalents of an alkali metal hydride in a polar solvent such as dimethylsulfoxide the desired compound of formula I.

Alternatively, the formula IVa intermediate can be protected using standard procedures such as acetylation in the presence of acetic anhydride to give the 1-acetyl-aryloxyindolinone of formula VII. The protected formula VII indolinone is bis-alkylated as described hereinabove to give the protected spiroindolinone of formula VIII which is then deprotected by simple acid hydrolysis to give the unsubstituted aryloxyspiroindolinone of formula IX. Said formula IX compound is then alkylated using standard procedures such as reaction with an alkylhalide in the presence of a base to form the desired formula I compound. The reaction scheme is illustrated in flow diagram II.

FLOW DIAGRAM II

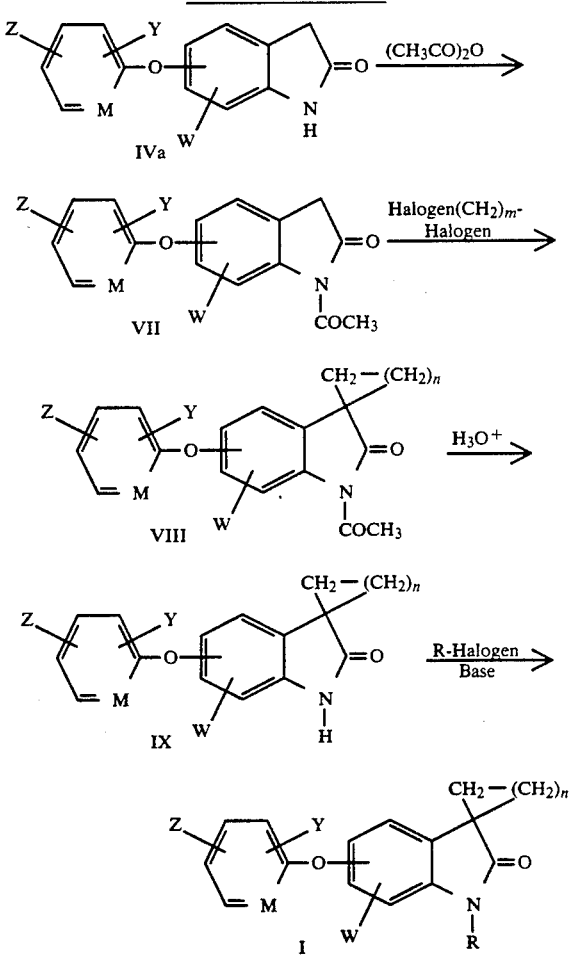

The aryloxy-1'-(substituted)-spiro[cycloalkane-1,3'-indolin]-2'-one compounds of the invention are highly effective herbicidal agents for the control of a wide variety of herbaceous and woody, annual and perennial, monocotyledenous and dicotyledenous plants. Said compounds are especially useful for the effective control of said plants in the presence of cereal crops such as rice and wheat.

The compounds of the invention are effective for controlling a wide variety of undesirable plant species when applied to the foliage thereof or to soil or water containing seeds or other propagating organs thereof such as tubers, rhizomes or stolons at rates of about 0.005 to 5.0 kg/ha. The compounds may be applied to the soil after planting, but prior to emergence, or to the soil and incorporated therein prior to planting or to the foliage and stems of plants after emergence.

The compounds of the invention are effective for controlling undesirable plant species including important weeds in transplanted rice culture. The compounds may be applied to the soil or water containing transplanted rice plants and seeds or other propagating organs of a variety of weed species or said compounds may be applied to soil or water containing directly seeded rice and seeds or other propagating organs of a variety of weed species or to the stems or foliage of the weed plants in the presence of rice plants.

The aryloxyspiroalkylindolinone compounds of the invention may be conveniently applied as a liquid or solid herbicidal composition comprising an admixture of an inert carrier or diluent and a herbicidally effective amount of a compound of formula I and optionally an adjuvant. Liquid herbicidal compositions may contain carriers and adjuvants such as organic solvents and water, as well as emulsifiers, stabilizers, dispersants, suspending agents, spreaders, penetrants, wetting agents and the like. Common solid carriers or diluents include clays, talc, diatomaceous earth, silica and the

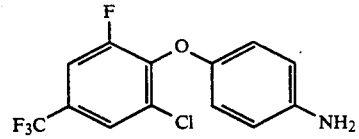

A rapidly stirred mixture of p-aminophenol (43.6 g, 0.40 mol), m-chloro-α,α,α,3,4-pentafluorotoluene (86.6 g, 0.40 mol) and potassium carbonate (82.8 g, 0.60 mol) in acetonitrile, under a nitrogen atmosphere, is heated at reflux temperature for 24 hours, cooled and diluted with a mixture of water and ether. The organic phase is separated, washed successively with water and brine. The aqueous phases are combined and extracted with ether. All organic phases are combined, dried over MgSO₄ and concentrated in vacuo to give the title product as a dark brown solid, 102.5 g (84%), mp 55–57° C.

Using essentially the same procedure and substituting m-chloro-α,α,α,4-tetrafluorotoluene as starting material, p-[(2-chloro-α,α,α-trifluorotolyl)oxy]aniline is obtained as a light brown solid, mp 65°–66.5° C.

EXAMPLE 2

Preparation of 5-[(2-Chloro-α,α,α,6-tetrafluorotolyl)oxy]-3-(methylthio)-2-indolinone

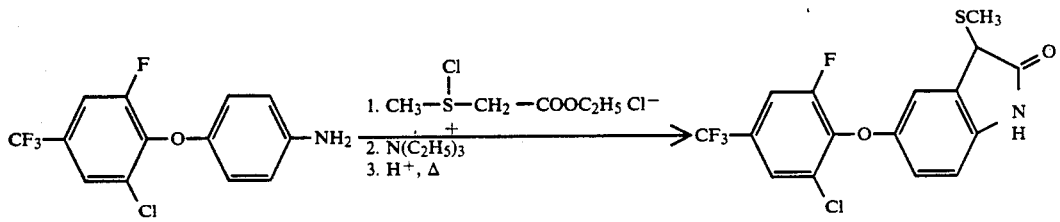

like. Preferred herbicidal compositions are those such as dispersible granulates, wettable powders, flowables or aqueous emulsifiable concentrates which can be diluted with water at the site of application. Further, dry compositions such as granules, dusts and the like may be used.

In order to facilitate a further understanding of the invention, the following examples are presented primarily for the purpose of illustrating certain more specific details thereof. The invention is not to be deemed limited thereby except as defined in the claims. The term ¹HNMR designates proton nuclear magnetic resonance spectroscopy.

EXAMPLE 1

Preparation of p-[(2-Chloro-α,α,α,6-tetrafluoro-p-tolyl)oxy]aniline

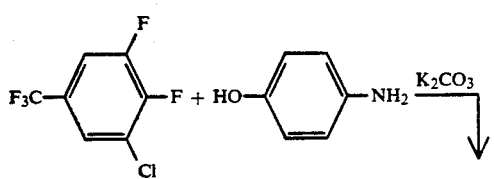

A solution of ethyl methylthioacetate (49.0 mL, 0.378 mol) in methylene chloride is added dropwise to a stirred solution of chlorine (19 mL, 0.412 mol) in methylene chloride at −70° C. over a 20 minute period. After stirring at −70° C. for 5 minutes, the reaction mixture is treated dropwise with a mixture of p-[(2-chloro-α,α,α-6-tetrafluoro-p-tolyl)oxy]aniline (105 g, 0.343 mol) and triethylamine (48 mL, 0.343 mol) in methylene chloride over a 45 minute period at −70° C., stirred for 1 hour, treated dropwise with neat triethylamine (83 mL, 0.60 mol), allowed to come to room temperature over a 2 hour period and diluted with water. The phases are separated and the aqueous phase is extracted further with methylene chloride. The organic phases are combined, dried over MgSO₄ and concentrated in vacuo to give a dark oil residue. The residue is dissolved in toluene, treated with p-toluenesulfonic acid (6.4 g, 0.037 mol), heated at reflux temperatures for 6 hours and cooled to room temperature. The resultant precipitate is filtered and air dried to give the title product as a tan solid, 51.6 g (38%), mp 137°–142° C.

Using essentially the same procedure and substituting p-[(2-chloro-α,α,α-trifluoro-p-tolyl)oxy]aniline as substrate, 5-[(2-chloro-α,α,α-trifluoro-p-tolyl)oxy]-3-(methylthio)-2-indolinone is obtained as a tan solid, mp 174.5°–178° C.

EXAMPLE 3

Preparation of
5-[(2-Chloro-α,α,α-trifluoro-p-tolyl)oxy]-2-indolinone

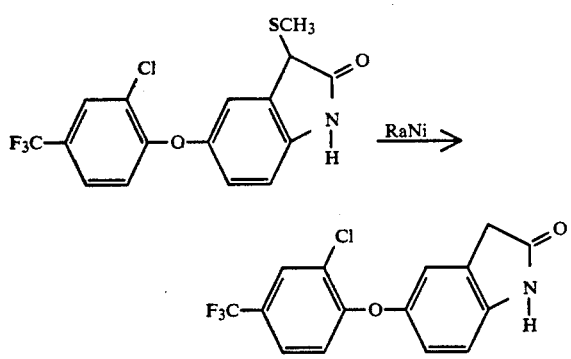

A stirred mixture of 5-[(2-chloro-α,α,α-trifluoro-p-tolyl)oxy]-3-(methylthio)-2-indolinone (25.0 g, 0.067 mol) in a 5:1 mixture of methanol and dimethylformamide is heated to 50° C., under a nitrogen atmosphere, treated portionwise with an aqueous slurry of Raney nickel W-2 catalyst until disulfurization is complete as determined by chromatography, cooled to room temperature and filtered through a bed of diatomaceous earth. The filtrate is concentrated in vacuo, diluted with a 1:1 mixture of ethyl acetate and ether, washed with water, dried over MgSO4 and reconcentrated in vacuo to afford the title product as a tan solid, 16.5 g (75%), identified by ¹HNMR analysis.

Using essentially the same procedure and employing 5-[(2-chloro-α,α,α,6-tetrafluoro-p-tolyl)oxy]-3-(methylthio)-2-indolinone as starting material, 5-[(2-chloro-α,α,α-6-tetrafluoro-p-tolyl)oxy]-2-indolinone is obtained as a tan solid, identified by ¹HNMR analysis.

EXAMPLE 4

Preparation of
5-[(2-Chloro-α,α,α,6-tetrafluoro-p-tolyl)-oxy]-1-methyl-2-indolinone

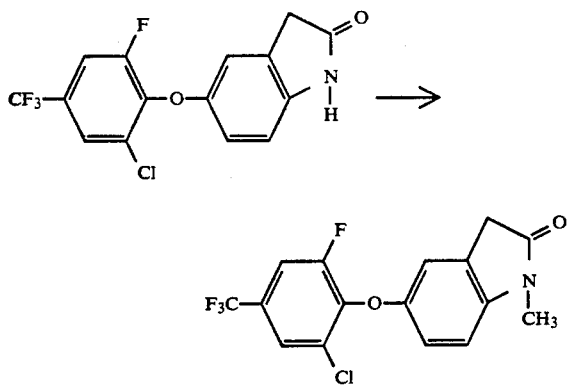

A solution of 5-[(2-chloro-α,α,α,6-tetrafluro-p-tolyl)oxy]-2-indolinone (16.8 g, 0.0485 mol) in toluene is treated in a single portion with a 60% sodium hydride dispersion in mineral oil (2.13 g, 0.0534 mol NaH) at 60° C., stirred for 30 minutes, treated dropwise with a solution of dimethylsulfate (5.1 mL, 0.0534 mol) in toluene over a 20 minute period at 60° C., stirred for 2 hours, cooled to room temperature and diluted with a mixture of ethyl acetate and water. The phases are separated, the organic phase is washed with brine and the aqueous phases are combined and further extracted with ethyl acetate. All organic phases are combined, dried over MgSO4, and concentrated in vacuo to give a light brown semi-solid residue. Trituration under a mixture of 3-5% ethyl acetate in hexane and filtration yields the title product as a light pink solid, 13.45 g (77%), mp 111°-112° C.

Using essentially the same procedure and employing 5-[(2-chloro-α,α,α,-trifluoro-p-tolyl)oxy]-2-indolinone as starting material, 5-[(2-chloro-α,α,α-trifluoro-p-tolyl)oxy]-1-methyl-2-indolinone is obtained as a beige solid in 65% yield, mp 180°-185° C.

EXAMPLE 5

Preparation of
5'-[(2-Chloro-α,α,α,6-tetrafluoro-p-tolyl)-oxy]-1,-methyl-spiro[cyclopropane-1,3'-indolinone]-2'-one

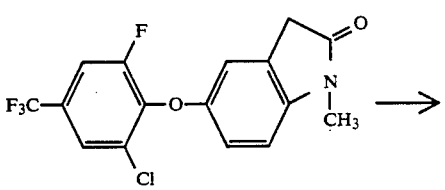

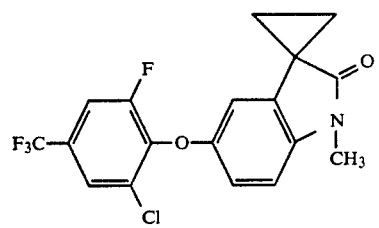

A solution of 5-[(2-chloro-α,α,α,6-tetra-fluoro-p-tolyl)oxy]-1-methyl-2-indolinone (13.4 g, 0.0372 mol) in dimethylsulfoxide is treated with a 60% dispersion of sodium hydride in mineral oil (3.28 g, 0.082 mol NaH) at room temperature in a single portion, stirred for 30 minutes, treated dropwise with a solution of 1,2-dibromoethane (7.70 g, 0.041 mol) in dimethylsulfoxide over a 45 minute period, stirred for hours and poured into a mixture of ethyl acetate and water. The phases are separated and the aqueous phase is extracted with ether. All organic phases are combined, dried over MgSO4 and concentrated in vacuo to afford a brown semi-solid residue. Trituration and chromatography affords the title product as a white solid, 7.70 g (54%), mp 128°-130° C.

Using essentially the same procedure and employing the appropriately substituted aryloxyindolinone and the appropriate dihaloalkane, the following compounds are obtained:

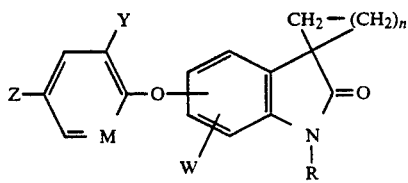

| M | Y | Z | R | W | n | % Yield | mp °C |
|---|---|---|---|---|---|---------|-------|
| C—Cl | H | CF3 | CH3 | H | 1 | 47 | 181–182 |

-continued

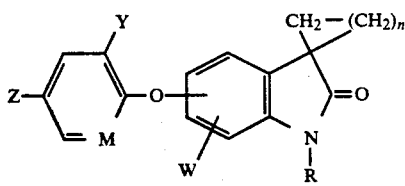

| M | Y | Z | R | W | n | % Yield | mp °C. |
|---|---|---|---|---|---|---|---|
| N | Cl | CF$_3$ | CH$_3$ | H | 1 | 44 | 138–141 |
| C—Cl | F | CF$_3$ | CH$_3$ | H | 3 | 63 | 106–109 |
| C—Cl | H | CF$_3$ | CH$_3$ | H | 3 | 50 | 109–111 |
| C—Cl | F | CF$_3$ | CH$_3$ | H | 4 | 62 | 102–105 |

EXAMPLE 6

Preparation of
5-[(2-Chloro-α,α,α,6-tetrafluoro-p-tolyl)oxy]-1-acetyl-2-indolinone

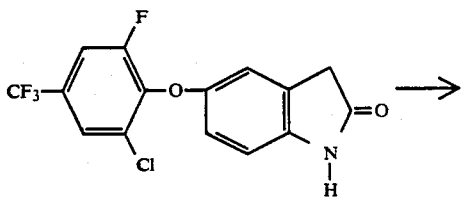

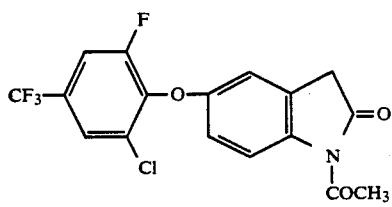

A mixture of 5-[(2-chloro-α,α,α,6-tetra-fluoro-p-tolyl)oxy]-2-indolinone (6.8 g, 18.9 mmol) in acetic anhydride is heated at reflux temperature with stirring for 30 minutes, cooled to room temperature and concentrated in vacuo to give a brown wet residue. The residue is re-evaporated twice using xylenes and chromatographed using 10% ethyl acetate in hexane to give the title product as a white solid, 5.1 g (67%), mp 119°–121° C., identified by $^1$HNMR.

EXAMPLE 7

Preparation of
5'-[(2-Chloro-α,α,α,6-tetrafluoro-p-tolyl)oxy]-1'-acetyl-spiro[cyclopropane-1,3-indolin]-2'-one

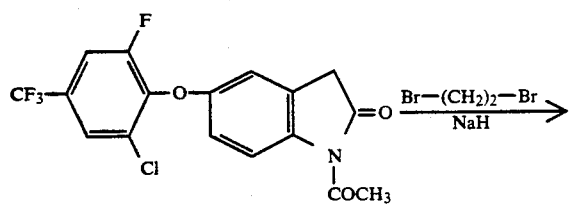

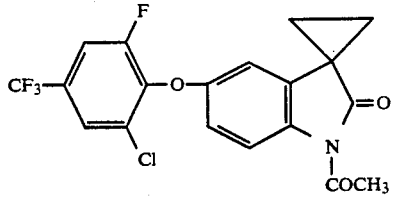

A solution of 5-[(2-chloro-α,α,α,6-tetrafluoro-p-tolyl)oxy]-1-acetyl-2-indolinone (5.1 g, 12.7 mmol) in dimethylsulfoxide is treated with sodium hydride (1.12 g, 27.9 mmol) portionwise over a 30 minute period, treated dropwise with a solution of 1,2-dibromoethane (2.62 g, 14.0 mmol) in dimethylsulfoxide over a 1 hour period and stirred at room temperature until reaction is complete by thin layer chromatography. The reaction mixture is poured into a mixture of water and ether, treated with 10% HCl and separated. The organic phase is washed with water, dried (MgSO$_4$) and concentrated in vacuo to give a residue. The residue is chromatographed on silica gel using 5–10% ethyl acetate in hexane to give the title product as a pale yellow solid, 1.1 g, (20%), mp 118.5°–121° C., identified by $^1$HNMR.

EXAMPLE 8

Preparation of 5'-[(2-Chloro-α,α,α,6-tetrafluoro-p-tolyl)oxy]-spiro[cyclopropane-1,3'-indolin]-2'-one

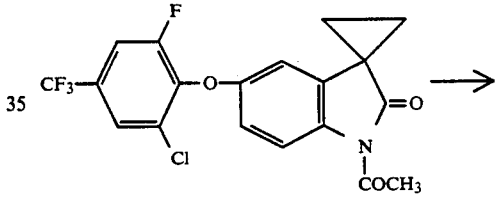

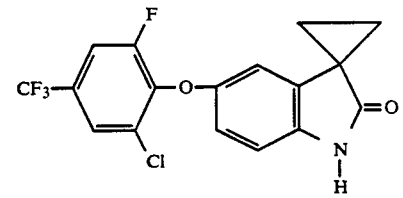

A mixture of 5'-[(2-chloro-α,α,α,6-tetrafluoro-p-tolyl)oxy]-1'-acetyl-spiro[cyclopropane-1,3'-indolin]-2'-one (0.60 g, 1.95 mmol), 5 mL of 1 N H$_2$SO$_4$ and tetrahydrafuran is heated at reflux for about 24 hours (until reaction is complete by gas chromatographic analysis). The reaction mixture is diluted with ethyl acetate and water and the phases are separated. The organic phase is dried (MgSO$_4$) and concentrated in vacuo to give a residue. The residue is chromatographed using silica gel and ethyl acetate/hexane 25/75 to give the title product as a white solid, 0.41 g, (76%), mp 168°–170° C. identified by H$^1$NMR.

EXAMPLE 9

Postemergence Herbicidal Evaluation of Test Compounds

The postemergence herbicidal activity of the compounds of the invention is demonstrated by the following tests wherein a variety of monocotyledonous and dicotyledonous plants are treated with test compounds dispersed in aqueous acetone mixtures. In the tests, seedling plants are grown in jiffy flats for about 2 weeks. The test compounds are dispersed in 50/50 acetone/water mixtures containing about 0.5% TWEEN® 20, a polyoxyethylene sorbitan monolaurate surfactant of Atlas Chemical Industries, in sufficient quantity to provide the equivalent of about 0.032 to 0.5 kg per hectare of active compound when applied to the plants through a spray nozzle operating at 40 psi for a predetermined time. After spraying, the plants are placed on greenhouse benches and are cared for in the manner commensurate with conventional greenhouse practices. From 1 to 2 weeks after treatment, the seedling plants are examined and rated according to the rating system provided below. The data obtained are shown in Table I.

The rating scale is based upon a visual observation of plant stand, vigor, malformation, size, chlorosis and overall plant appearance as compared with a control.

| Rating | | % Control (Compared to Check) |
|---|---|---|
| 9 | Complete kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |

Plant Species Used

| Column Heading | Common Name | Scientific Name |
|---|---|---|
| Barnyard gr | Barnyardgrass | ECHINOCHLOA CRUS-GALLI, (L) BEAU |
| Large Crab | Crabgrass, (hairy) Large | DIGITARIA SANGUINALIS, (L) SCOP |
| Green Fox | Foxtail, Green | SETARIA VIRIDIS, (L) BEAUV |
| Milet Pros | Millet, Proso | PANICUM MILIACEUM, L. |
| Mrnglry Sp | Morningglory Spp | IPOMOEA SPP. |
| Pigweed Sp | Pigweed Spp. | AMARANTHUS SPP. |
| Ragweed | Ragweed, Common | AMBROSIA ARTEMISIIFOLIA, L. |
| Velvetleaf | Velvetleaf | ABUTILON THEOPHRASTI, MEDIC. |
| Corn Field | Corn, Field | ZEA MAYS, L. |
| Rice Uplnd | Rice Upland | ORYZA SATIVA, L. |
| Soybean | Soybean | GLYCINE MAX, (L) MERR. |
| W Wheat XX | Wheat, Winter, XXX | TRITICUM AESTIVUM, L. |

TABLE I

| | | Postemergence Herbicidal Evaluation of Test Compounds | | | | | | | | | | |
|---|---|---|---|---|---|---|---|---|---|---|---|---|
| Compound | Rate kg/ha | Barn-yard gr | Large crab | Green fox | Millet pros | Mrngl ry Sp | Pig-weed sp | Rag weed | Velvet leaf | Corn field | Rice uplnd | Soy bean | W Wheat XX |
| 5'-[(2-chloro-alpha,alpha,alpha-trifluoro-p-tolyl)oxy]-1'-methyl-spiro-[cyclopentane-1,3'-indolin]-2'-one | 0.500 | 2 | 9 | 6 | 5 | 8 | 9 | 8 | 9 | 4 | 2 | 7 | 3 |
| | 0.125 | 0 | 5 | 0 | 1 | 5 | 9 | 6 | 9 | 0 | 0 | 3 | 0 |
| | 0.032 | 0 | 0 | 0 | 0 | 6 | 5 | 2 | 5 | 0 | 0 | 1 | 0 |
| 5'-[(2-chloro-alpha,alpha,alpha-6-tetrafluoro-p-tolyl)oxy]-1'-methyl-spiro-[cyclopentane-1,3'-indolin]-2'-one | 0.500 | 2 | 7 | 7 | 6 | 8 | 9 | 9 | 9 | 3 | 0 | 3 | 1 |
| | 0.125 | 5 | 9 | 8 | 7 | 9 | 9 | 9 | 9 | 4 | 0 | 4 | 1 |
| | 0.032 | 3 | 7 | 6 | 6 | 8 | 9 | 9 | 8 | 2 | 0 | 3 | 0 |
| 5'-[(2-chloro-alpha,alpha,alpha-6-tetrafluoro-p-tolyl)oxy]-1'-methyl-spiro-[cyclohexane-1,3'-indolin]-2'-one | 0.500 | 3 | 9 | 8 | 8 | 9 | 9 | 9 | 9 | 4 | 4 | 7 | 4 |
| | 0.125 | 4 | 7 | 2 | 6 | 8 | 9 | 8 | 9 | 4 | 1 | 6 | 3 |
| | 0.032 | 3 | 7 | 4 | 5 | 9 | 9 | 6 | 7 | 2 | 2 | 7 | 2 |
| 5'-[(2-chloro-alpha,alpha,alpha-6-tetrafluoro-p-tolyl)oxy]-1'-methyl-spiro-[cyclopropane-1,3'-indolin]-2'-one | 0.500 | 9 | 9 | 9 | 9 | 9 | 9 | 9 | 9 | 4 | 8 | 9 | 8 |
| | 0.125 | 8 | 9 | 9 | 9 | 9 | 9 | 9 | 9 | 8 | 4 | 8 | 6 |
| | 0.032 | 6 | 9 | 7 | 8 | 9 | 9 | 9 | 9 | 4 | 2 | 7 | 3 |
| 5'-[(2-chloro-alpha,alpha,alpha-trifluoro-p-tolyl)oxy]-1'-methyl-spiro-[cyclopropane-1,3'-indolin]-2'-one | 0.500 | 1 | 1 | 1 | 1 | 8 | 9 | 5 | 9 | 1 | 1 | 2 | 1 |
| | 0.125 | 1 | 0 | 0 | 0 | 9 | 9 | 2 | 8 | 1 | 0 | 2 | 0 |
| | 0.032 | 0 | 0 | 0 | 0 | 9 | 9 | 2 | 5 | 0 | 0 | 1 | 0 |

EXAMPLE 10

Preemergence Herbicidal Evaluation of Test Compounds

The preemergence herbicidal activity of the compounds of the invention is exemplified by the following tests in which the seeds of a variety of monocotyledenous and dicotyledenous plants are separately mixed with potting soil and planted on top of about one inch of soil in jiffy flats. After planting, the flats are sprayed with selected aqueous acetone solutions containing test compound in sufficient quantity to provide the equivalent of about 0.500 kg/ha of test compound per flat. The treated flats are then placed on greenhouse benches and cared for in accordance with conventional greenhouse procedures. From 2 to 3 weeks after treatment, the flats are examined and the plants are rated according to the rating system set forth above. The herbicidal proficiency and crop selectivity of the compounds of the invention is evident from the data obtained and shown in Table II.

cm above the soil surface. At intervals of 0 to 12 days after transplanting, and seeding, the flooded soil surface of the cups are treated with the selected aqueous acetone solution containing test compound in sufficient quantity to provide the equivalent of about 0.008 to 1.0 kg per hectare of test compound per cup. The treated cups are then placed on greenhouse benches, watered such that the water level is maintained as stated above and cared for in accordance with conventional greenhouse practice. Three to five weeks after treatment, the tests are terminated and each cup is examined and rated according to the rating system provided in Example 9.

TABLE II

| | | | Preemergence Herbicidal Evaluation of Test Compounds | | | | | | | | | | |
|---|---|---|---|---|---|---|---|---|---|---|---|---|---|
| Compound | Rate kg/ha | Barn-yard gr | Large crab | Green fox | Millet pros | Mrngl ry Sp | Pig-weed sp | Rag weed | Velvet leaf | Corn field | Rice uplnd | Soy bean | W Wheat XX |
| 5'-[(2-chloro-alpha,alpha,alpha-trifluoro-p-tolyl)oxy]-1'-methyl-spiro-[cyclopentane-1,3'-indolin]-2'-one | 0.500 | 0 | 6 | 7 | 2 | 3 | 5 | 2 | 0 | 0 | 0 | 0 | 0 |
| 5'-[(2-chloro-alpha,alpha,alpha-6-tetrafluoro-p-tolyl)oxy]-1'-methyl-spiro-[cyclopentane-1,3'-indolin]-2'-one | 0.500 | 2 | 9 | 9 | 8 | 9 | 9 | 8 | 9 | 2 | 0 | 4 | 3 |
| 5'-[(2-chloro-alpha,alpha,alpha-6-tetrafluoro-p-tolyl)oxy]-1'-methyl-spiro-[cyclohexane-1,3'-indolin]-2'-one | 0.500 | 0 | 9 | 9 | 3 | 9 | 9 | 3 | 4 | 0 | 0 | 0 | 0 |
| 5'-[(2-chloro-alpha,alpha,alpha-6-tetrafluoro-p-tolyl)oxy]-1'-methyl-spiro-[cyclopropane-1,3'-indolin]-2'-one | 0.500 | 9 | 9 | 9 | 9 | 9 | 9 | 9 | 9 | 9 | 1 | 9 | 8 |
| 5'-[(2-chloro-alpha,alpha,alpha-trifluoro-p-tolyl)oxy]-1'-methyl-spiro-[cyclopropane-1,3'-indolin]-2'-one | 0.500 | 0 | 2 | 3 | 2 | 3 | 9 | 0 | 0 | 0 | 0 | 0 | 0 |

EXAMPLE 11

Preemergence and Postemergence Herbicidal Evaluation In The Presence of Translanted Rice The selectivity of the compounds of the invention is exemplified by the following tests in which 2 ten-day old rice seedlings are transplanted into a 32 oz plastic container with a diameter of 10.5 cm containing 700 g of a silt loam soil. Barnyardgrass seeds are planted in the top 0.5-1.0 cm of soil. After planting, the containers are flooded and the water level is maintained at 0.5 to 3.0

The data obtained are reported in Table III below.

| | Plant Species Used | |
|---|---|---|
| Column Heading | Common Name | Scientific Name |
| Barnydgr | Barnyardgrass | Echinochloa crus-galli, (L) beau |
| Rice Tebon | Rice CV. Tebonnet | Oryza sativa, (L) tebonnet |

TABLE III

| | | Herbicidal Evaluation In The Presence Of Transplanted Rice | | | | | | | | |
|---|---|---|---|---|---|---|---|---|---|---|
| | | Time Of Herbicide Application (Days After Transplanting) | | | | | | | | |
| | | 0 | | 3 | | 6 | | 9 | | 12 | |
| Compound Name | Rate kg/ha | Barn ydgr | Rice Tebon | Barn ydgr | Rice Tebon | Barn ydgr | Rice Tebon | Barn ydgr | Rice Tebon | Barn ydgr | Rice Tebon |
| 5'-[(2-chloro- | 1.00 | 9 | 2 | 9 | 2 | 9 | 2 | 9 | 2 | 8 | 2 |
| alpha,alpha,alpha- | 0.500 | 9 | 2 | 9 | 2 | 9 | 2 | 9 | 2 | 9 | 2 |
| 6-tetrafluoro- | 0.250 | 9 | 2 | 9 | 2 | 9 | 2 | 9 | 2 | — | 2 |
| p-tolyl)oxy]-1'- | 0.125 | 9 | 2 | 9 | 2 | 9 | 2 | 5 | 2 | 4 | 2 |

TABLE III-continued

| | | Herbicidal Evaluation In The Presence Of Transplanted Rice | | | | | | | | |
|---|---|---|---|---|---|---|---|---|---|---|
| | | Time Of Herbicide Application (Days After Transplanting) | | | | | | | | |
| | | 0 | | 3 | | 6 | | 9 | | 12 |
| Compound Name | Rate kg/ha | Barn ydgr | Rice Tebon | Barn ydgr | Rice Tebon | Barn ydgr | Rice Tebon | Barn ydgr | Rice Tebon | Barn ydgr | Rice Tebon |
| methyl-spiro-[cyclopropane-1,3'-indolin]-2'-one | 0.063 | 9 | 2 | 9 | 2 | 8 | 2 | 2 | 2 | 1 | 2 |
| | 0.032 | 9 | 1 | 9 | 1 | 7 | 1 | 2 | 1 | 0 | 1 |

EXAMPLE 12

Preemergence Herbicidal Evaluation In The Presence of Transplanted Rice

The selectivity of the compounds of the invention is exemplified by the following tests in which 2 ten-day old rice seedlings are transplanted into a 32 oz plastic container with a diameter of 10.5 cm containing 700 g of a silt loam soil. Seeds of important weed species in transplanted rice culture are planted in the top 0.5–1.0 cm of soil. After planting, the containers are flooded and the water level is maintained at 0.5 to 3.0 cm above the soil surface. Three to seven days after transplanting, the flooded soil surface of the cups are treated with the selected aqueous acetone solution containing test compound in sufficient quantity to provide the equivalent of about 0.016 to 0.250 kg per hectare of test compound per cup. The treated cups are then placed on greenhouse benches, watered such that the water level is maintained as stated above and cared for in accordance with conventional greenhouse practice. Three to five weeks after treatment, the tests are terminated and each cup is examined and rated according to the rating system provided in Example 9. The data obtained are reported in Table IV below.

| Plant Species Used | | |
|---|---|---|
| Column Heading | Common Name | Scientific Name |
| Pyg Arowhd | Arrowhead (Pygmaea) Jap. | Sagittaria pygmaea, L. |
| Barnydgr | Barnyardgrass | Echinochloa crus-galli, (L) beau |
| Flatsedge | Flatsedge, Jap. | Cyperus serotinus, Rottb. |
| Rice Koshi | Rice CV. Koshihikari | Oryza sativa |

TABLE IV

Preemergence Herbicidal Evaluation In The Presence Of Transplanted Rice

| Compound Name | Rate kg/ha | Rice Koshi | Barn ydgr | Pyg Ar owhd | Flat sedge |
|---|---|---|---|---|---|
| 5'-[(2-Chloro-α,α,α,6-tetra-fluoro-p-tolyl)-oxy]-1'-methyl-spiro[cyclo-propane-1,3'-indole]-2'-one | 0.250 | 1 | 9 | 8 | 9 |
| | 0.125 | 1 | 9 | 6 | 9 |
| | 0.063 | 1 | 9 | 4 | 9 |
| | 0.032 | 0 | 9 | 4 | 9 |

EXAMPLE 13

Postemergence Herbicidal Evaluation Under Flooding Conditions

The postemergence herbicidal activity of the compounds of the invention under flooding conditions commonly used in rice culture in North and South American countries is demonstrated by the following tests wherein a variety of plant species are grown in 32 oz plastic containers with a diameter of 10.5 cm containing 700 g of a silt loam soil. The seedling plants are grown for about 2 weeks, then treated with test compounds dispersed in aqueous acetone mixtures as described in Example 6. After the plants are treated, one-half of the containers are flooded and the water level is maintained at 0.5 to 3.0 cm above the soil surface. The treated cups are then placed on greenhouse benches, watered such that the water level is maintained as stated above and cared for in accordance with conventional greenhouse procedures.

The tests are terminated 3–5 weeks after treatment and evaluated and rated according to the rating system provided in Example 9. The data obtained are shown in Table V.

| Plant Species Used | | |
|---|---|---|
| Column Heading | Common Name | Scientific Name |
| Barnydgr | Barnyardgrass | Echinochloa crus-galli, (L) beau |
| Uplnd Rice | Upland Rice | Oryza sativa, L. |

TABLE V

Postemergence Herbicidal Evaluation Under Flooding Conditions

| | | Flooded | | Not Flooded | |
|---|---|---|---|---|---|
| Compound Name | Rate kg/ha | Barn ydgr | Uplnd rice | Barn ydgr | Uplnd rice |
| 5'-[(2-Chloro-α,α,α,6-tetra-fluoro-p-tolyl)-oxy]-1'-methyl-spiro[cyclo-propane-1,3'-indole]-2'-one | 0.250 | 4 | 9 | 5 | 9 |
| | 0.125 | 4 | 9 | 4 | 8 |
| | 0.063 | 2 | 9 | 2 | 3 |
| | 0.032 | 1 | 3 | 1 | 0 |

What is claimed is:

1. A compound having the structure

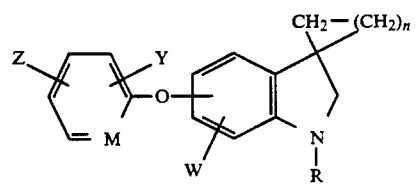

wherein
M is N or CX;
X, Y and Z are each independently hydrogen, halogen, CN, $NO_2$ or $C_1-C_6$ alkyl optionally substituted with one or more halogens;

W is hydrogen, halogen, CN, $NO_2$, $C_1-C_6$ alkoxy, $C_1-C_6$ carboalkoxy or $C_1-C_6$ alkyl optionally substituted with one or more halogens or $OR_1$ groups with the proviso that at least two of W, X, Y and Z must be other than CN or $NO_2$;

n is an integer of 1, 2, 3, 4 or 5;

R is $C_3-C_6$ alkenyl, $C_3-C_6$ alkynyl or $C_1-C_6$ alkyl optionally substituted with one or more halogens, $OR_1$, $COOR_1$ or $NH_2$ groups;

$R_1$ is hydrogen or $C_1-C_4$ alkyl.

2. The compound according to claim 1 wherein M is CX.

3. The compound according to claim 2, wherein X and Y are halogen and Z is $CF_3$.

4. The compound according to claim 2 5'-[(2-chloro-$\alpha,\alpha,\alpha$,6-tetrafluoro-p-tolyl)oxy]-1'-methyl-spiro[cyclopropane-1,3'-indolin]-2'-one.

5. The compound according to claim 2 5'-[(2-chloro-$\alpha,\alpha,\alpha$,-trifluoro-p-tolyl)oxy]-1'-methyl- spiro[cyclopropane-1,3'-indolin]-2'one.

6. The compound according to claim 2 5'-[(2-chloro-$\alpha,\alpha,\alpha$,6-tetrafluoro-p-tolyl)oxy]-1'- methyl-spiro[cyclopentane-1,3'-indolin]-2'-one.

7. The compound according to claim 2 5'-[(2-chloro-$\alpha,\alpha,\alpha$,-trifluoro-p-tolyl)oxy]-1'-methyl-spiro- [cyclopentane-1,3'-indolin]-2'-one.

8. The compound according to claim 2 5'-[(2-chloro-$\alpha,\alpha,\alpha$,6-tetrafluoro-p-tolyl)oxy]-1'- methyl-spiro[cyclohexane-1,3'-indolin]-2'-one.

9. A method for the control of moncotyledonous and dicotyledenous plant species which comprises applying to the foliage of said plants or to the soil or water containing seeds or other propagating organs of said plants a herbicidally effective amount of an aryloxyspiroalkylindolinone as described in claim 1.

10. A herbicidal composition which comprises an inert solid or liquid diluent and a herbicidally effective amount of a compound having the structure as described in claim 1.

11. The method according to claim 9 wherein said compound is as described in claim 2.

12. The method according to claim 11 wherein said compound is as described in claim 3.

13. The method according to claim 9 wherein the undesirable plant species are selectively controlled in the presence of a cereal crop.

14. The method according to claim 13 wherein the cereal crop is rice or wheat.

15. A method for the selective control of undesirable monocotyledenous and dicotyledenous plant species in the presence of transplanted rice which comprises applying to the flood water or soil as a preemergence post-transplant or pre-plant incorporated treatment a herbicidally effective amount of a compound described in claim 1.

16. The method according to claim 15 wherein said compound is as described in claim 2.

17. The method according to claim 15 wherein the compound is applied to the flood water or soil at a rate of about 0.005 to 5.0 kg/ha.

* * * * *